(12) United States Patent
Grigoryants et al.

(10) Patent No.: US 7,125,413 B2
(45) Date of Patent: Oct. 24, 2006

(54) ENDOSCOPIC FUNDOPLICATION DEVICES AND METHODS FOR TREATMENT OF GASTROESOPHAGEAL REFLUX DISEASE

(75) Inventors: Sergey S. Grigoryants, Arlington, MA (US); Liem T. Vu, Needham, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 542 days.

(21) Appl. No.: 10/175,307

(22) Filed: Jun. 20, 2002

(65) Prior Publication Data
US 2003/0236536 A1    Dec. 25, 2003

(51) Int. Cl.
*A61B 17/08* (2006.01)
*A61B 17/10* (2006.01)
*A61B 17/04* (2006.01)

(52) U.S. Cl. ............................ 606/153; 606/139

(58) Field of Classification Search ............. 606/153, 606/139, 142, 148, 151, 74, 228, 223, 232, 606/144; 600/104; 24/16 PB, 30.5 R, 30.5 P, 24/3.13, 116 R, 116 A, 704.2; 604/95.01
See application file for complete search history.

(56) References Cited

U.S. PATENT DOCUMENTS

| | | | | |
|---|---|---|---|---|
| 3,072,986 A | * | 1/1963 | Lefnaer | 24/16 PB |
| 3,086,265 A | * | 4/1963 | Orenick et al. | 24/16 PB |
| 3,123,077 A | | 3/1964 | Alcamo | |
| 3,570,497 A | * | 3/1971 | Lemole | 606/151 |
| 3,597,803 A | * | 8/1971 | Van Neil | 24/16 PB |
| 3,830,538 A | * | 8/1974 | Moberg | 24/704.2 |
| 3,973,299 A | * | 8/1976 | Keefe | 24/16 PB |
| 3,985,138 A | | 10/1976 | Jarvik | |
| 4,069,825 A | | 1/1978 | Akiyama | |
| 4,214,349 A | * | 7/1980 | Munch | 24/16 PB |
| 4,711,002 A | * | 12/1987 | Kreeger | 24/30.5 P |
| 4,950,285 A | * | 8/1990 | Wilk | 606/232 |
| 4,994,073 A | | 2/1991 | Green | |
| 5,085,661 A | | 2/1992 | Moss | |
| 5,088,979 A | | 2/1992 | Filipi et al. | |
| 5,123,913 A | * | 6/1992 | Wilk et al. | 606/232 |
| 5,207,694 A | * | 5/1993 | Broome | 606/148 |
| 5,222,976 A | * | 6/1993 | Yoon | 606/223 |
| 5,285,944 A | | 2/1994 | Green et al. | |
| 5,330,503 A | | 7/1994 | Yoon | |
| 5,500,000 A | * | 3/1996 | Feagin et al. | 606/232 |
| 5,527,322 A | | 6/1996 | Klein et al. | |
| 5,607,389 A | | 3/1997 | Edwards et al. | |
| 5,713,908 A | | 2/1998 | Jameel et al. | |
| 5,843,121 A | | 12/1998 | Yoon | |

(Continued)

FOREIGN PATENT DOCUMENTS

DE    43 02 895 A1    8/1994

(Continued)

OTHER PUBLICATIONS

PCT International Search Report for International Application No. PCT/US03/18935, Mailed on Mar. 3, 2004.

*Primary Examiner*—Julian W. Woo
(74) *Attorney, Agent, or Firm*—Finnegan Henderson Farabow Garrett & Dunner, L.L.P.

(57) ABSTRACT

Endoscopic devices and methods used for fastening multiple tissue layers, such as, for example, an endoscopic fundoplication procedure, are disclosed. The endoluminal device includes a tissue fastener, a flexible needle having means for grasping and releasing a portion of the tissue fastener, and a deflector for deflecting and guiding the needle toward the multiple tissue layers.

30 Claims, 12 Drawing Sheets

U.S. PATENT DOCUMENTS

| | | |
|---|---|---|
| 5,897,562 A | 4/1999 | Bolanos et al. |
| 5,910,105 A | 6/1999 | Swain et al. |
| 6,086,600 A | 7/2000 | Kortenbach |
| 6,113,609 A | 9/2000 | Adams |
| 6,152,934 A | 11/2000 | Harper et al. |
| 6,190,353 B1 * | 2/2001 | Makower et al. ........ 604/95.01 |
| 6,231,561 B1 | 5/2001 | Frazier et al. |
| 6,241,748 B1 | 6/2001 | Adams |
| 6,736,828 B1 * | 5/2004 | Adams et al. .............. 606/213 |
| 2001/0039426 A1 | 11/2001 | Makower et al. |

FOREIGN PATENT DOCUMENTS

| | | |
|---|---|---|
| DE | 44 47 658 C2 | 11/1995 |
| WO | WO 99/48429 | 9/1999 |
| WO | WO 00/78227 A1 | 12/2000 |
| WO | WO 02/24080 A2 | 3/2002 |

* cited by examiner

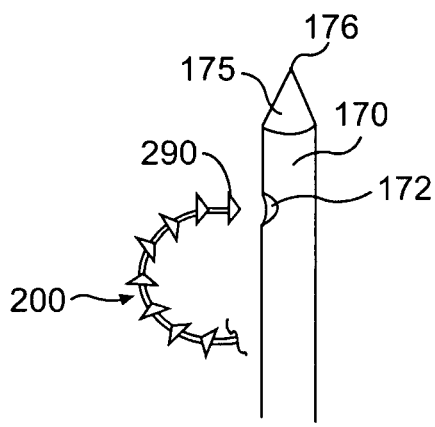
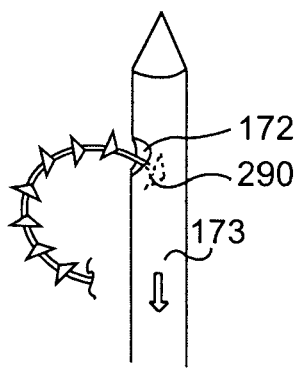
FIG. 3A  FIG. 3B
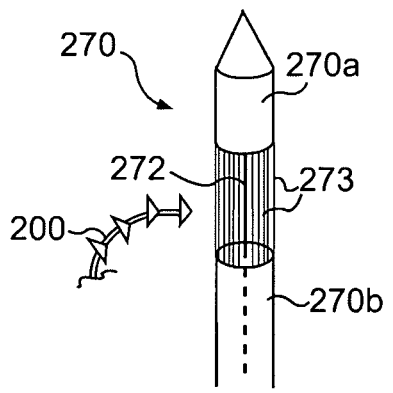
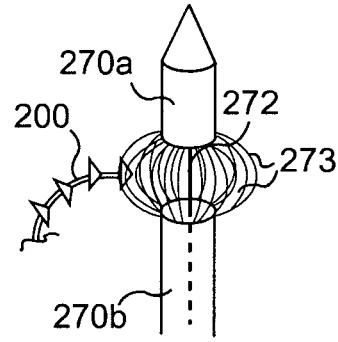
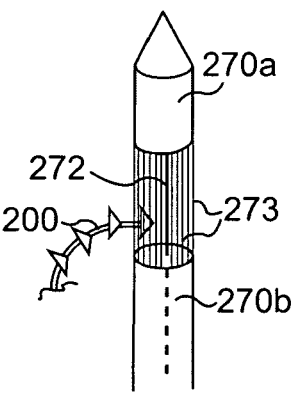
FIG. 4A  FIG. 4B  FIG. 4C
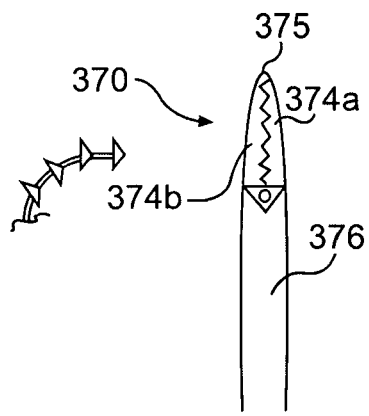
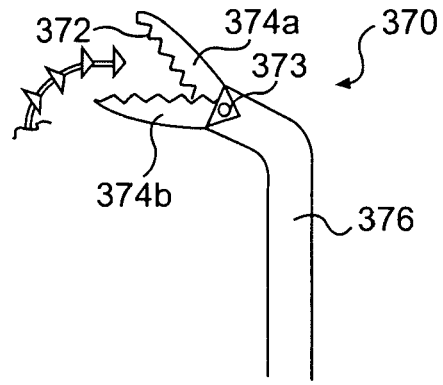
FIG. 5A  FIG. 5B

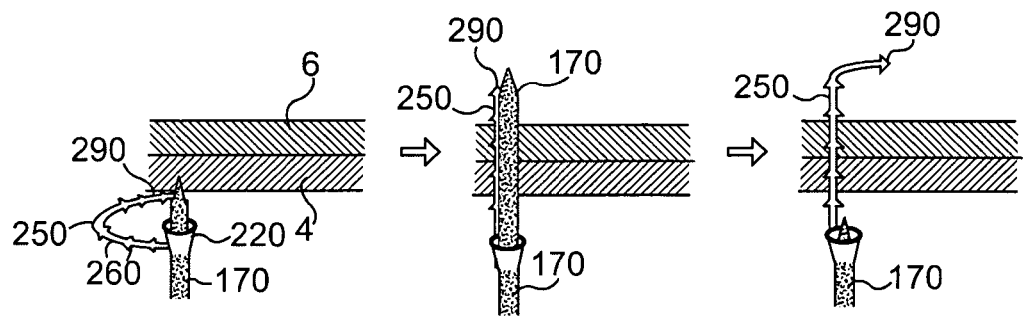
FIG. 17   FIG. 18   FIG. 19
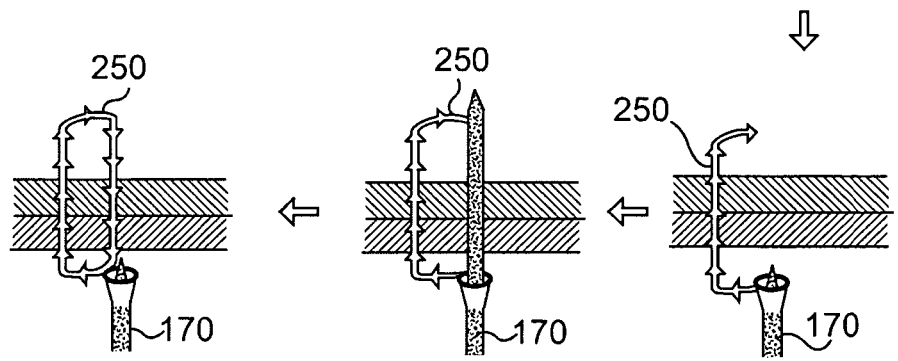
FIG. 22   FIG. 21   FIG. 20
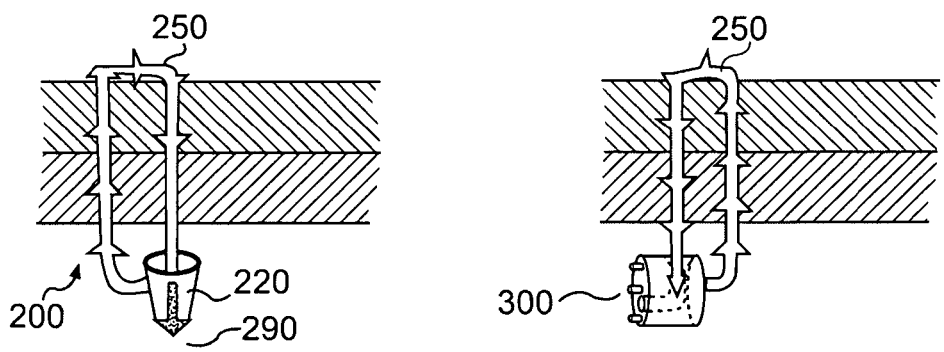
FIG. 23   FIG. 24

ENDOSCOPIC FUNDOPLICATION DEVICES AND METHODS FOR TREATMENT OF GASTROESOPHAGEAL REFLUX DISEASE

DESCRIPTION OF THE INVENTION

1. Field of the Invention

The present invention relates to endoscopic devices and related methods. In particular, the present invention relates to endoscopic devices and methods used in, for example, an endoscopic fundoplication procedure for treatment of Gastroesophageal Reflux Disease (GERD).

2. Background of the Invention

Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES). With reference to FIG. 1A, the LES 2 is a ring of smooth muscle and increased annular thickness existing in approximately the last four centimeters of the esophagus. In its resting state, the LES creates a region of high pressure (approximately 15–30 mm Hg above intragastric pressure) at the opening of the esophagus 3 into the stomach 7. This pressure essentially closes the esophagus 3 so that contents of the stomach cannot pass back into the esophagus 3. The LES 2 opens in response to swallowing and peristaltic motion in the esophagus, allowing food to pass into the stomach. After opening, however, a properly functioning LES 2 should return to the resting, or closed state. Transient relaxations of the LES 2 do occur in healthy individuals, typically resulting in occasional bouts of heartburn.

The physical interaction occurring between the gastric fundus 5 and the esophagus 3 also prevents gastroesophageal reflux. The gastric fundus 5 is a lobe of the stomach situated at the top of the stomach 7 distal to the esophagus 3. In asymptomatic individuals, the fundus 5 presses against the opening of the esophagus 3 when the stomach 7 is full of food and/or gas. This effectively closes off the esophageal opening to the stomach 7 and helps to prevent acid reflux back into the esophagus 3. More specifically, as the food bolus is immersed in gastric acid, it releases gas which causes the fundus 5 of the stomach 7 to expand and thereby exert pressure on the distal esophagus 3 causing it to collapse. The collapse of the esophagus lumen reduces the space for the stomach acid to splash past the closed esophagus lumen and thereby protect the proximal esophagus from its destructive contact.

In individuals with GERD, the LES 2 functions abnormally, either due to an increase in transient LES relaxations, decreased muscle tone of the LES 2 during resting, or an inability of the esophageal tissue to resist injury or repair itself after injury. These conditions often are exacerbated by overeating, intake of caffeine, chocolate or fatty foods, smoking, and/or hiatal hernia. Avoiding these exacerbating mechanisms helps curb the negative side effects associated with GERD, but does not change the underlying disease mechanism.

A surgical procedure, known generally as fundoplication, has been developed to prevent acid reflux in patients whose normal LES functioning has been impaired, either as a result of GERD or other adverse effects. This procedure involves bringing the fundus wall 6 into closer proximity of the esophageal wall 4 to help close off the esophageal opening into the stomach 7, as shown in FIG. 1B. Traditionally, this procedure has been performed as an open surgery, but also has been performed laparoscopically.

As with any surgery, the attendant risks are great. Due to relatively large incisions necessary in the performance of open surgery, relatively large amount of blood is lost, the risk of infection increases, and the potential for post-operative hernias is high. Further, the relatively large incisions necessary in the performance of open surgery require extended recovery times for the incision to heal.

A laparoscopic procedure may involve performing laparotomies for trocar ports (penetrations of the abdominal wall), percutaneous endoscopic gastronomies (incisions through the skin into the stomach), and the installation of ports through which, for example, a stapler, an endoscope, and an esophageal manipulator (invagination device) are inserted. Under view of the endoscope, the esophageal manipulator is used to pull the interior of the esophagus 3 into the stomach 7. When the esophagus is in position, with the fundus 5 of the stomach plicated, the stapler is moved into position around the lower end of the esophagus and the plicated fundus is stapled to the esophagus 3. The process may be repeated at different axial and rotary positions until the desired fundoplication is achieved. This procedure is still relatively invasive requiring incisions through the stomach, which has a risk of infection. The location of the incision in the abdominal wall presents a risk of other negative effects, such as sepsis, which can be caused by leakage of septic fluid contained in the stomach.

SUMMARY OF THE INVENTION

Therefore, it is accordingly an object of the present invention to provide less invasive devices and methods for performing the fundoplication procedure. This is achieved by utilizing tissue fasteners and related deployment systems which can be endoluminally delivered through the esophagus, thereby eliminating the need for highly invasive, physiologically insulting surgical procedures.

To attain the advantages and in accordance with the purpose of the invention, as embodied and broadly described herein, one aspect of the invention provides an endoluminal surgical device for fastening multiple tissue layers. The device includes a tissue fastener, a flexible needle having means for grasping and releasing a portion of the tissue fastener, and a deflector for deflecting and guiding the needle toward the multiple tissue layers.

Another aspect of the present invention is to provide a tissue fastener used to join multiple tissue layers. The tissue fastener includes a flexible suture having a distal end and a proximal end, and a locking mechanism configured to interconnect the distal end and the proximal end to form the suture into a closed loop.

In yet another aspect of the present invention, a tissue fastener used to join multiple tissue layers is provided. The tissue fastener includes a connecting member, a distal fastening member, and a proximal fastening member. The distal fastening member is fixedly coupled to a distal portion of the connecting member, and the proximal fastening member is moveably coupled to the connecting member proximate a proximal portion of the connecting member. After the multiple tissue layers are placed between the distal and proximal fastening members, the proximal fastening member is moved relative to the connecting member to adjust a tension of the tissue fastener.

In still another aspect of the present invention, a method of fastening multiple tissue layers using a tissue fastener having a distal end and a proximal end is provided. The method includes providing a needle having a sharp distal end, attaching the distal end of the tissue fastener to the needle, passing the needle and the distal end of the tissue fastener through a first location of the tissue layers from a first side of the tissue layers to a second side of the tissue layers, while keeping the proximal end of the suture on the first side, releasing the distal end of the tissue fastener from the needle, withdrawing the needle through the tissue layers, passing the needle to the second side through a second location of the tissue layers, attaching the distal end of the tissue fastener to the needle, withdrawing the needle and the distal end of the tissue fastener through the tissue layers to the first side, and interconnecting the distal end and the proximal end of the tissue fastener to form a closed loop.

In still another aspect of the present invention, a method of fastening multiple tissue layers using a tissue fastener having a distal member, a proximal member, and a connecting member connecting the distal and proximal members, is provided. The method includes extending a tube within the multiple tissue layers from a first side of the tissue layers to a second side of the tissue layers, placing a tissue fastener inside the tube, passing the distal member of the tissue fastener to the second side through the tube while holding the proximal member on the first side, expanding the distal member against a surface of the tissue layers, and exposing the proximal member out of the tube on the first side, and expanding the proximal member against a surface of the multiple tissue layers.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

In the drawings:

FIGS. 3A–3B are perspective views of a needle basket, according to an embodiment of the present invention, illustrating operational steps for grasping a distal end of a suture;

FIG. 4A–4C are perspective views of a needle basket, according to another embodiment of the present invention, illustrating operational steps for grasping a distal end of a suture;

FIG. 5A–5B are perspective views of biopsy forceps used as a needle basket, according to still another embodiment of the present invention, illustrating operational steps for grasping a distal end of a suture;

FIGS. 17–22 are schematic illustrations of a method of fastening multiple tissue layers, according to an embodiment of the present invention;

FIG. 23 is a cross sectional view of two layers of tissue, with a tissue fastener in place, according to an embodiment of the present invention;

FIG. 24 is a cross sectional view of two layers of tissue, with a tissue fastener in place, according to another embodiment of the present invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1A:
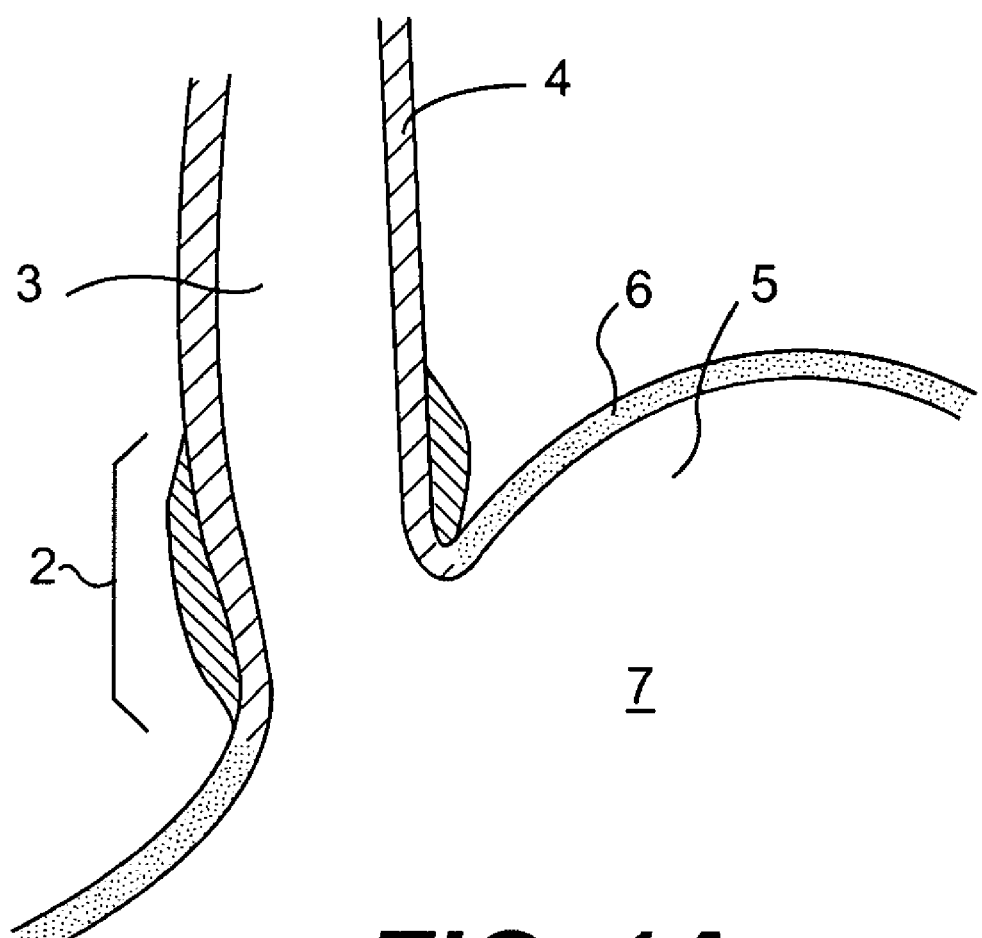
FIG. 1A is a cross-sectional view of the gastrointestinal tract in the region of the lower esophageal sphincter (LES) and the fundus of the stomach.
Figure 1B:
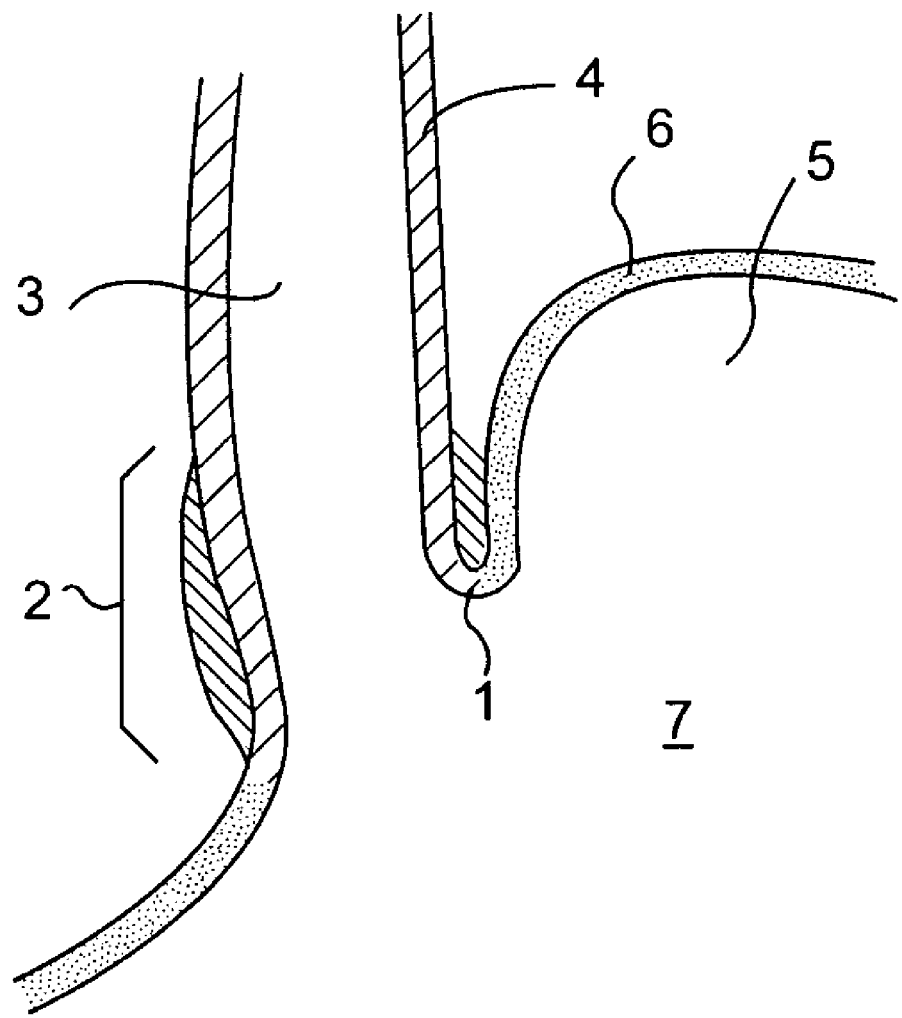
FIG. 1B is a cross-sectional view of the gastrointestinal tract in the region of the lower esophageal sphincter (LES) and the fundus of the stomach, after a fundoplication procedure is performed.

A newly developed form of fundoplication, referred to as endoscopic fundoplication, is an endoluminal procedure in which the fundus wall 6 is folded back onto the esophagus wall 4, as shown in FIG. 1B. The tissue fold 1 formed between the esophagus 3 and the fundus 5 then is secured. Endoscopic fundoplication is intended to be performed as an endoluminal procedure in which insertion of required medical instruments occurs through the esophagus 3. Such a procedure has the benefits of being less invasive, quicker, and less expensive as compared to previous techniques.

Figure 2:
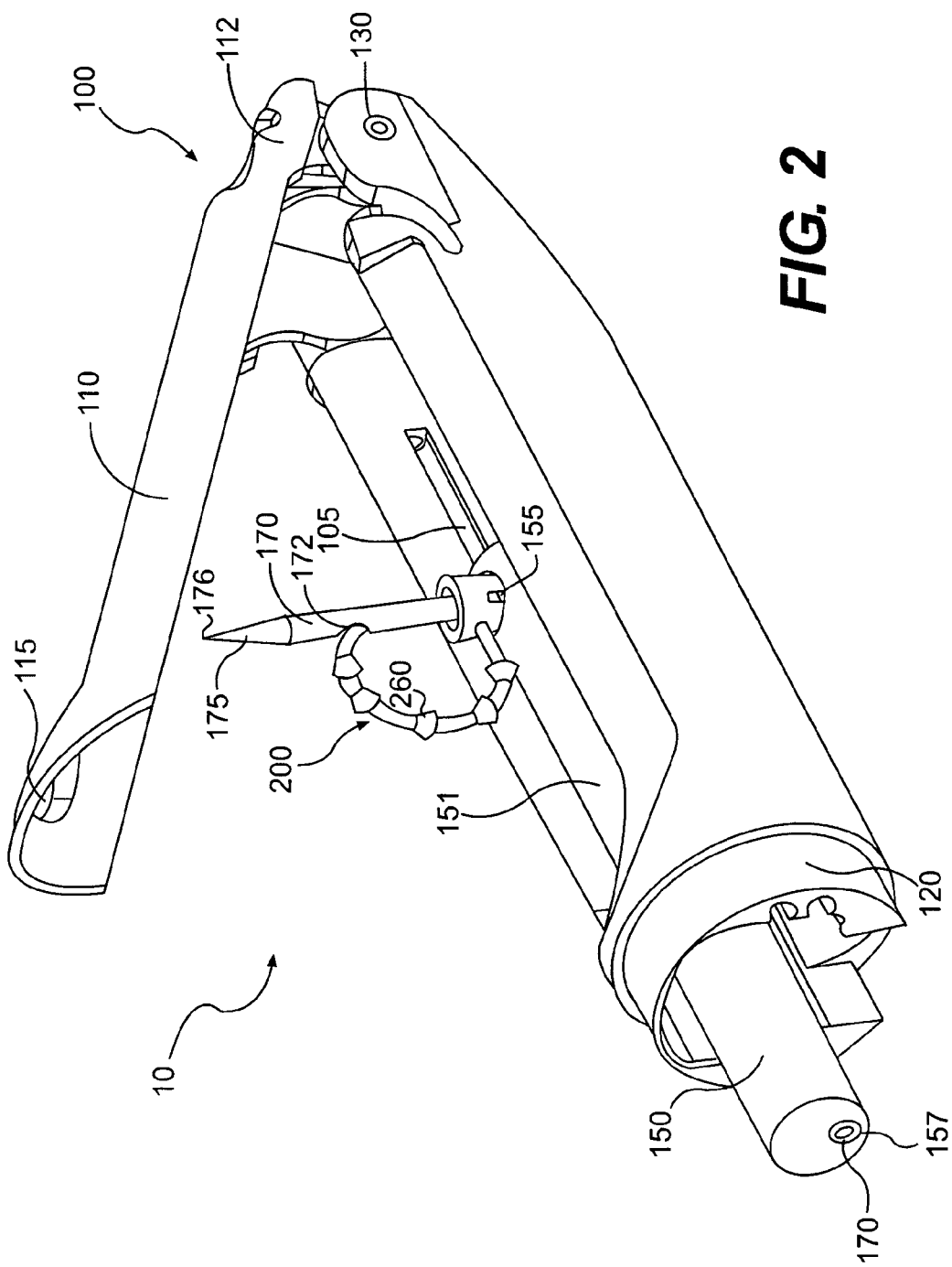
FIG. 2 is a perspective view of a distal portion of an endoscopic fundoplication device, according to an embodiment of the present invention.

FIG. 2 shows a distal portion of an exemplary endoluminal surgical device 10 employed in, for example, a fundoplication procedure, according to an embodiment of the present invention. The device 10 includes a flexible tube 120 that can extend from outside of a body to a site deep within the body. The tube 120 is a relatively flexible multilumened tube, designed to encompass various operating devices, such as, for example, endoscopes and graspers, and related cables for manipulating the operating devices. The tube 120 provides sufficient flexibility for traversing through tortuous paths within the body, for example, to the grastroesophageal junction site.

As shown in FIG. 2, the endoluminal device 10 includes A-frame head 100 coupled to a distal portion of the tube 120. A-frame head 100 is a relatively short cylindrical tube with a folding arm 110, a proximal end 112 of which is pivotally connected to a distal end of the A-frame head 100. The folding arm 110 is rotatable with respect to a pivot member 130, such that, in a contracted state, the folding arm 110 is folded in flush with an outer surface of the A-frame head 100 and, in an extended state, the folding arm 110 rotatably extends to receive multiple tissue layers to be folded between the folding arm 110 and the side surface of the A-frame head 100. For example, the A-frame 100 with the folding arm 110 is configured to fold the gastric fundus wall 6 proximate to the esophageal wall 4 to make a plication fold 1. The folding arm 110 has an opening 115 or a slot along its length to permit passage of a needle basket 170 and a tissue fastener 200. Wires, cables, or other suitable mechanisms (not shown) for manipulating the folding arm 110 run through lumens of the tube 120. The proximal end of that mechanism connects to any suitable actuator known in the art at the proximal end of device 10. Preferably, an endoscope (not shown) is placed proximate to the A-frame head 100 for viewing. The device 10 may also include a grasper device (not shown) configured to grasp the esophageal wall 4 during the folding process to prevent possible tissue movement. Preferably, the grasper device is a suction grasper having a suction cup positioned inside the A-frame head 100. The suction grasper device uses an air suction mechanism to grasp the esophageal wall 4. Any other conventionally known fundoplication devices that may be used in conjunction with device 10 to aid in the fundoplication procedure, such as those described in U.S. Pat. No. 6,086,600, the disclosure of which is hereby incorporated by reference, may be utilized.

During delivery, the A-frame head 100 is preferably covered with a A-frame protection device (not shown) formed of a thin membrane tubing. The protection device has a through opening for an endoscope to protrude and move forward from the distal end of the A-frame head 100. The protection device protects the esophageal wall 4 from possible damage during delivery.

Figure 7:
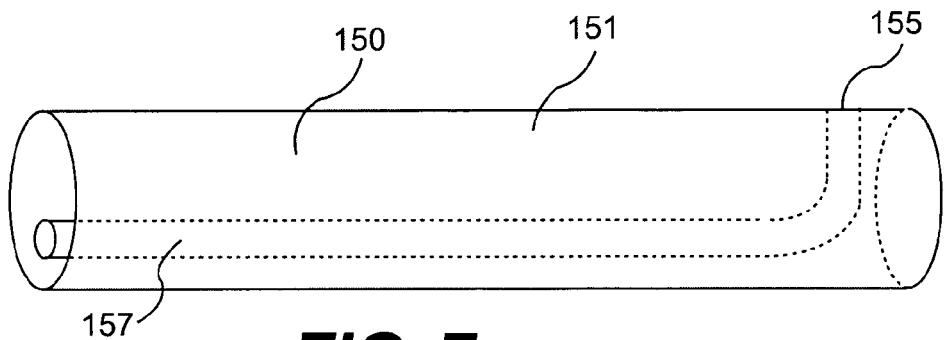
FIGS. 7–9 are schematic illustration of a deflector, a needle basket, and a tissue fastener arrangement, according to an embodiment of the present invention.

The endoluminai device 10 further includes a long, catheter-like deflector 150 disposed inside the tube 120. Preferably, a proximal end (not shown) of the deflector 150 extends outside of a body to facilitate manipulation of the deflector 150. Any suitable actuation device known in the art may be employed at the proximal end of deflector 150. The deflector 150 is configured to move axially within the A-frame head 100 via a slot 105 formed in the A-frame head 100 in the axial direction. The deflector 150 includes a conduit 157 formed inside the deflector 150, which extends substantially axially within the deflector 150 to the outside of the body. The conduit 157 provides a path within the deflector 150 through which a needle basket 170 moves relative to the deflector 150. The conduit 157 is curved in the distal portion of the deflector 150, substantially perpendicular to the side surface 151 of the deflector 150, as shown in FIG. 7, such that the needle basket 170 is guided to exit the deflector 150 through a side opening 155 formed on the side surface 151 of the deflector 150. It should be understood that the conduit 157 may be curved by more or less than 90° angle, depending on the direction to which the needle basket 170 is desired to be deflected.

The needle basket 170 used for perforating through multiple tissue layers is substantially flexible, yet rigid enough to penetrate through the multiple tissue layers, and includes a sharp cutting edge 175 and/or a needle point 176 at its distal end. Preferably, a proximal end (not shown) of the needle basket 170 extends to outside a body to facilitate movement of the needle basket 170 relative to the deflector 150. Any suitable actuator known in the art may be employed at the proximal end of the device 10 to move the needle basket 170.

The needle basket 170 includes means for grasping and releasing the distal end 290 of a suture 250, located proximate the distal end of the needle basket 170. FIGS. 3A–3B show a portion of the needle basket 170 having means for grasping and releasing the distal end 290 of a suture 250, according to an embodiment of the present invention. In this embodiment, the means for grasping and releasing includes a suction hole 172 and a suction conduit 173 formed inside the hollow needle basket 170. Similar to the suction grasper device described above, the needle basket 170 uses air suction mechanism to draw the distal end 290 of the suture 150 inside the suction hole 172. Preferably, the proximal end of the needle basket 170 is connected to a suitable suction device (not shown). By turning on and off the suction device, the distal end 290 of the suture 250 can be easily grasped or released.

FIGS. 4A–4C show a needle basket 270 having a basket type grasping and releasing means, according to another embodiment of the present invention. The needle basket 270 includes a distal portion 270a and a proximal portion 270b, interconnected by an actuation wire 272 and a plurality of basket wires 273. The actuation wire 272 is fixedly attached to the distal portion 270a and axially moveable relative to the proximal portion 270b of the needle basket 270 to cause axial movement of the distal portion 270a with respect to the proximal portion 270b. The actuation wire 272 is substantially flexible, yet rigid enough to move the distal portion 270a of the needle basket 270 without bending. The basket wires 273 are also made of flexible and rigid material, yet made less rigid than the actuation wire 272. Preferably, the basket wires 273 are formed of shape memory materials. As shown in FIGS. 4A and 4C, when the distal and proximal portions 270a, 270b are separated apart by the length of the basket wires 273, the basket wires 273 form substantially straight wires that are aligned substantially parallel to each other. The space between the basket wires 273 at this stage is smaller than the cross-sectional area of the suture distal end 290. As shown in FIG. 4B, when the distal and proximal portions 270a, 270b of the needle basket 270 are moved toward each other by pulling the actuation wire 272, the basket wires 273 are bent outwardly and widen the space between the basket wires 273, permitting the distal end 290 of the suture 250 to enter the space. At this point, the distal and proximal portions 270a, 270b of the needle basket 270 are then again separated apart so that the distal end 290 of the suture 250 is firmly secured inside the cylindrical space formed by the plurality of basket wires 273.

FIGS. 5A–5B show biopsy forceps used as a needle basket 370, according to still another embodiment of the present invention. The needle basket 370 includes a pair of biopsy jaws 374a, 374b, joined together by a pivot pin 373 and positioned at the distal end of a flexible elongated tubular member 376. The distal end portion of the tubular member 376 is freely moveable with respect to a main body portion of the tubular member 376 and preferably deflectable in different angles, as shown in FIG. 5B. When the pair of biopsy jaws 374a, 374b are closed, as shown in FIG. 5A, the needle basket 370 forms a sharp cutting edge 375 on its distal end for perforating multiple tissue layers. The jaws 374a, 374b can be closed and opened to grasp and release the distal end 290 of the suture 250 by suitable actuation means employable at the proximal end of the tubular member 376.

It should be understood that any other needle basket designs having similar configuration may be utilized for the needle basket 170, such as, for example, baskets used in stone treatment or a flexible trocar tube.

Figure 6:
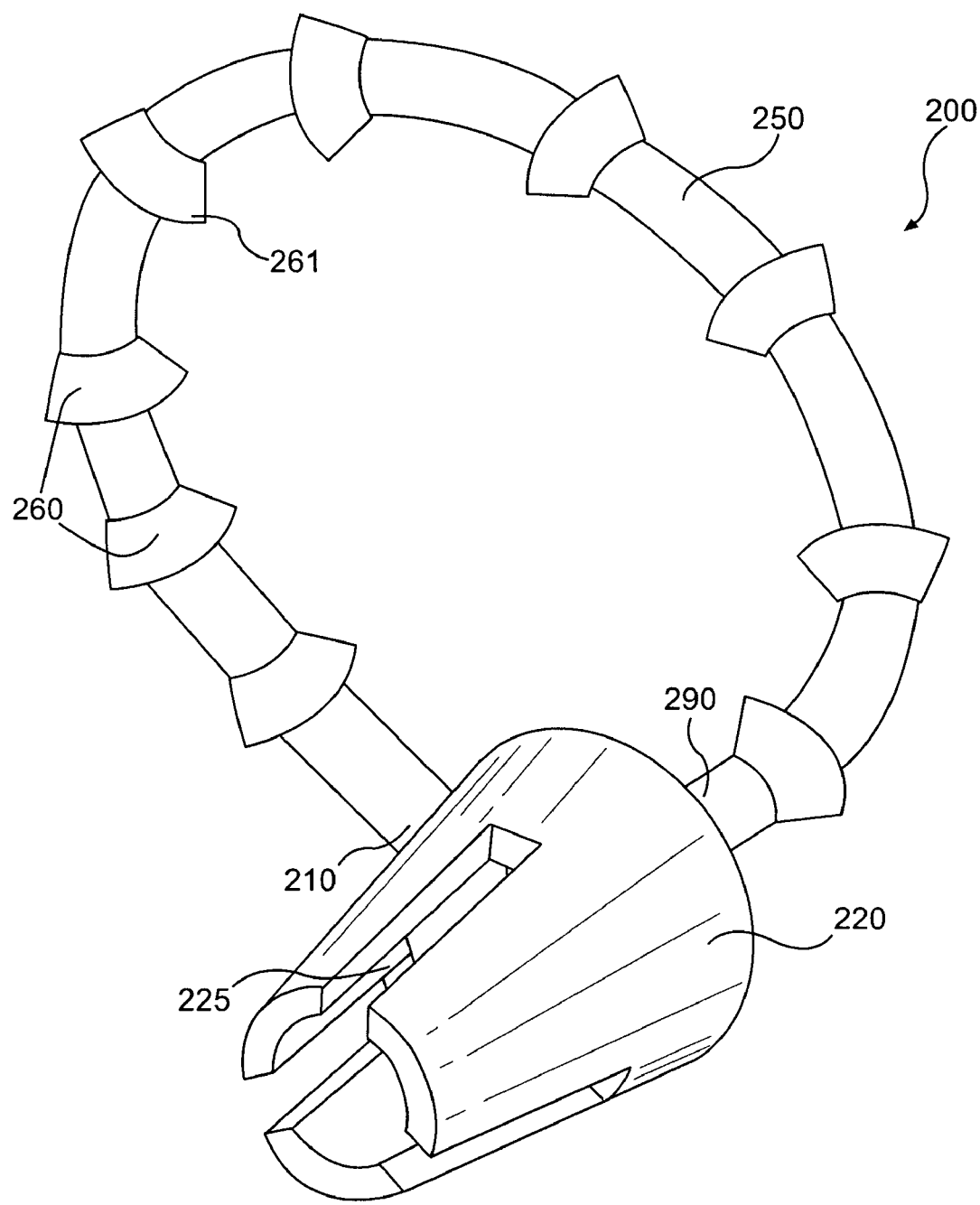
FIG. 6 is a perspective view of a tissue fastener according to an embodiment of the present invention.
Figure 8:
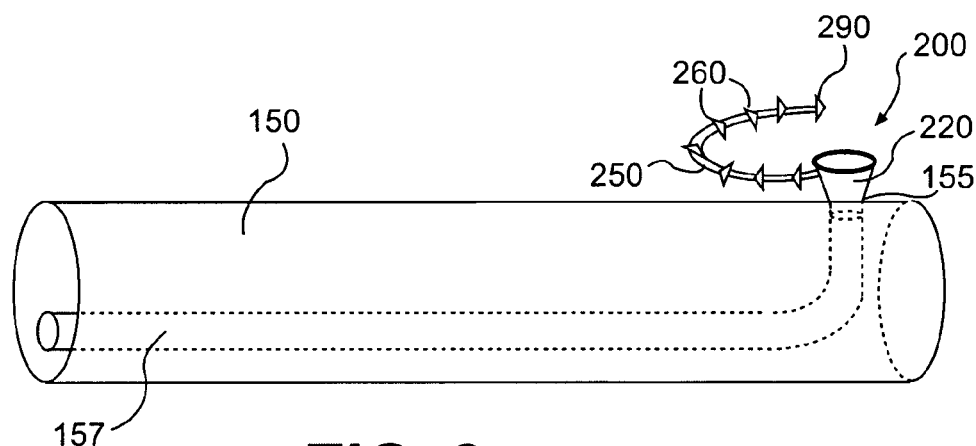

The side opening 155 of deflector 150 is configured to receive a tissue fastener 200, as shown in FIG. 8. FIG. 6 shows a tissue fastener 200 according to an embodiment of the present invention. The tissue fastener 200 includes a flexible suture 250 or tube with a locking mechanism 220 fixedly attached to the proximal end 210 of the suture 250. Preferably, the tissue fastener 200 may be formed of synthetic materials, such as ABS, polystyrene, polyurethane, PLLA, PLGA, nylon, and teflon. The tissue fastener can be made of biodegradable, bioresorbable, and/or bioabsorbable material, such that, as the fastener degrades, scar tissue forms and holds the tissue layers together. This erosion can occur in a controlled fashion by carefully selecting a material with a predetermined degradation rate. The bioabsorbable material may be formed of cross-linked polymer networks that can be manufactured to be responsive to body temperature, light, pH, and/or a number of other external/internal stimuli.

The suture 250 includes a plurality of locking flanges 260, preferably, spaced uniformly apart. When the suture 250 with the locking flanges 260 is inserted into the locking mechanism 220, the locking flange 260 is locked with the locking mechanism 220 to form a closed suture loop, as shown in FIG. 6. Preferably, the locking flanges 260 are configured to permit movement only in one direction when one of the locking flanges 260 is engaged with the locking mechanism 220. Movement of the suture 250 in one direction allows the adjustment of the fastening tension of the suture for fastening multiple tissue layers, while preventing undesirable loosening or release of the suture 250 from the locking mechanism 220. In addition to providing a locking function, the locking flanges 260 provide enhanced friction, preferably in one direction, when the suture 250 is placed within the tissue layers, such that the suture 250 is not easily dislocated. In this particular embodiment, each locking flange 260 is formed of a skirt-like or frustoconical-shaped ratchet 260. Preferably, each of the locking flanges 260 is defined by a slanted side surface 261 to provide the locking function and the enhanced friction, discussed above. Preferably, a proximal end of the locking mechanism 220 includes a plurality of slits 225 for providing the proximal end with a enhanced flexibility during placement in the opening 155 of the deflector 150. In particular, when the locking mechanism 220 is placed in the opening 155, the proximal end of the locking mechanism 220 is flexibly deformed to fit into the opening 155, while exerting an expansion force that makes the proximal end of the locking mechanism 220 stay in place within the opening 155. However, it should be understood that any other suitable designs of the locking flanges and the locking mechanism, which provide similar functions, may be utilized.

Figure 9:
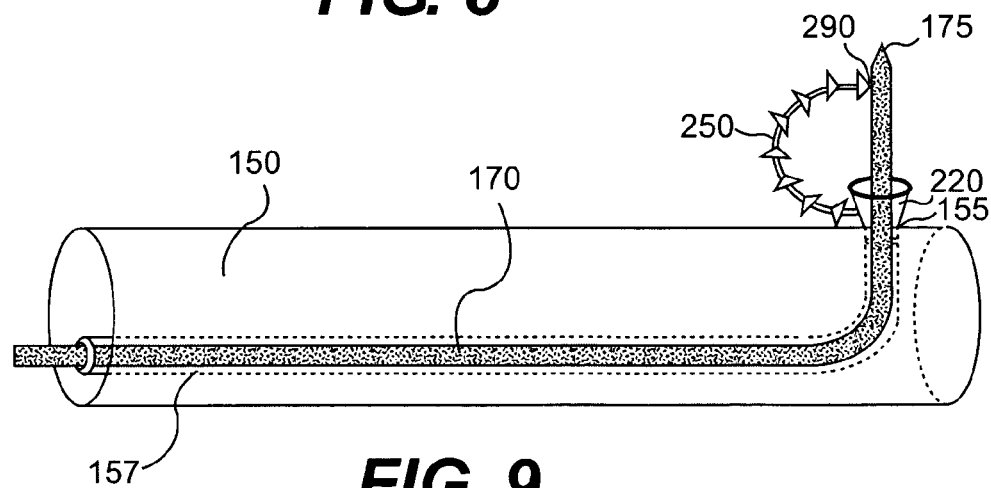

With reference to FIGS. 7–9, operation of the needle basket 170 in connection with a deflector 150, according to an embodiment of the present invention, is discussed herein. For illustration purpose, the needle basket 170 shown in FIGS. 3A–3B is used to describe its operation in connection with the deflector 150. It should be understood, however, that other embodiments of the needle baskets 270, 370 shown in FIGS. 4A–4C and 5A–5B, respectively, can also be used in similar manner described herein. As shown in FIG. 7, the deflector 150 includes a conduit 157 formed inside the deflector 150, through which a needle basket 170 travels relative to the deflector 150. The conduit 157 is bent substantially perpendicular to the side surface 151 in the distal portion of the deflector 150. On the side surface 151 of the deflector 150, an opening 155 configured to receive the tissue fastener 200 shown in FIG. 6 is formed. Any other suitable tissue fasteners with similar configuration may be used. As shown in FIG. 9, a flexible needle basket 170 is inserted through the conduit 157 of the deflector 150. The needle basket 170 is guided and deflected in the deflector 150 to perforate through multiple tissue layers. During a fundoplication procedure, for example, the endoluminal device 10 is inserted transorally to the lower end of the esophagus and, once the esophageal wall 4 and the fundus wall 6 are folded together, the deflector 150 with the needle basket 170 is inserted through a lumen of the endoluminal device 10. The needle basket 170 is then deflected inside of the deflector 150 and directed toward the folded layers of the esophageal wall 4 and the fundus wall 6 to perform perforation through the layers.

When the needle basket 170 protrudes out of the side opening 155 and through the locking mechanism 220 of the tissue fastener 200, the needle basket 170 grasps the distal loose end 290 of the suture 150 by the grasping and releasing means, described above, and carries it through the multiple tissue layers, as shown in FIG. 9.

Figure 10:
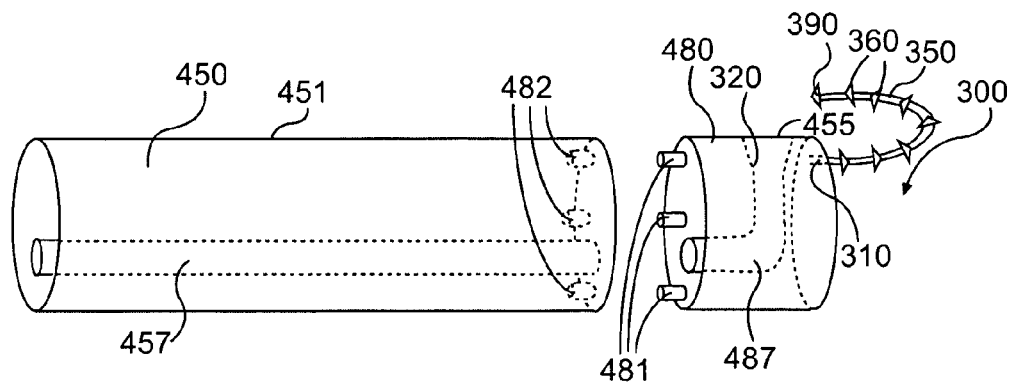
FIGS. 10–12 are schematic illustration of a deflector, a needle basket, and a tissue fastener arrangement, according to another embodiment of the present invention.
Figure 11:
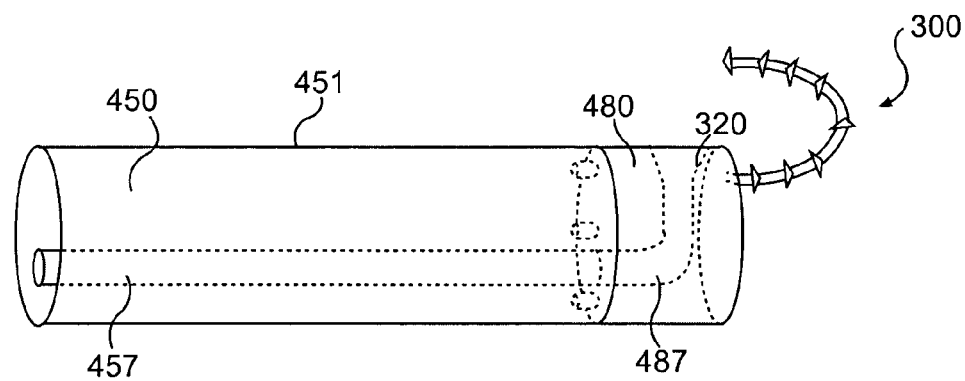
Figure 12:
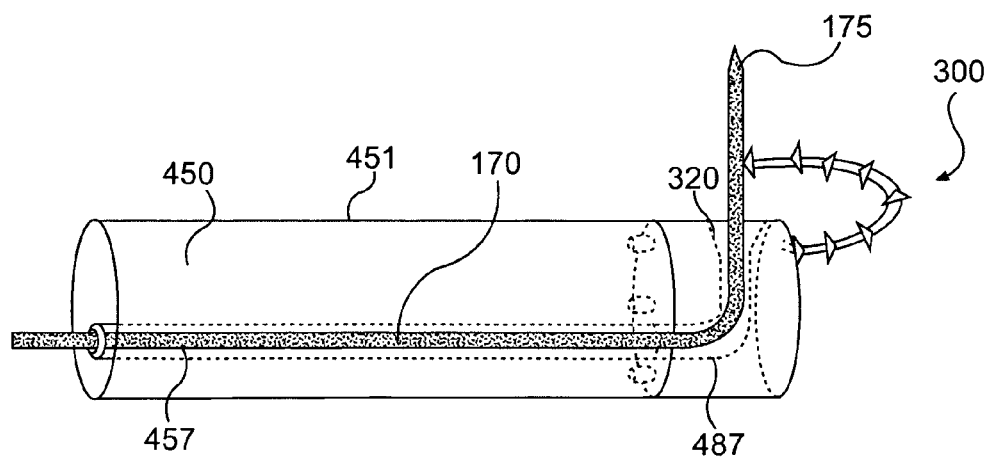

FIGS. 10–12 show a tissue fastener 300 and a deflector 450 according to another embodiment of the present invention. As shown in the figures, a distal portion 480 of a deflector 450 is releaseably coupled to the main body of the deflector 450 and constitutes a portion of the tissue fastener 300. While, in this particular embodiment, the distal portion 480 is coupled to the main body of the deflector 450 by a plurality of locking protrusions 481 configured to be mated with a plurality of respective recesses 482, any other suitable connection means can be utilized. Preferably, the connection means also includes releasing means to permit distal portion 480 to release from the remainder of deflector 450. The distal portion 480 and the main body of the deflector 450 is connected in such a way that a conduit 457 formed inside the main body communicates with a conduit 487 formed inside the distal portion 480. The conduit 487 formed in the distal portion 480 of the deflector 450 is bent substantially perpendicular to the side surface 451, and an opening 455 is formed on the side surface of the distal portion 480 of the deflector 450. As shown in the figures, a locking mechanism 320 for the tissue fastener 300 is disposed proximate to the opening 455. Preferably, the locking mechanism 320 is integrally formed with the conduit 487 of the distal portion 480. The tissue fastener 300 includes a flexible suture 350 or tube, a distal end of which is fixedly attached to the distal portion 480 of the deflector 450. The same type of suture 250 and locking mechanism 220 depicted in the embodiment shown in FIGS. 6–9 are used in this embodiment for illustration purpose and, therefore, further explanation of the suture 350 and locking mechanism 320 is omitted. It should be understood that this is, by no means, limiting and that any other suitable designs of the tissue fasteners and related locking mechanisms can be utilized.

Methods of installing the tissue fastener 200, 300, according to embodiments of the present invention, are described herein. For illustration purpose, the method is described in connection with a fundoplication procedure performed in the gastro-esophageal junction.

Figure 13:
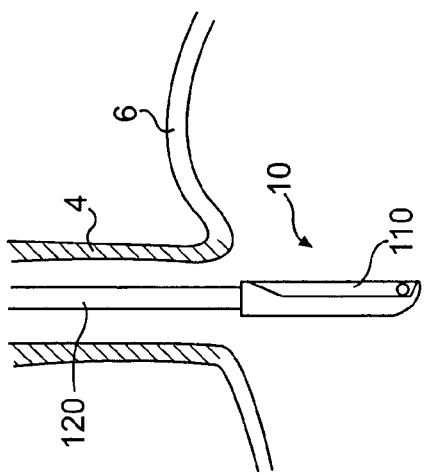
FIGS. 13–16 are schematic illustrations of the endoscopic fundoplication device shown in FIG. 2 in the gastro-esophageal junction, showing operational procedures for creating a plicated fold, according to an embodiment of the present invention.
Figure 14:
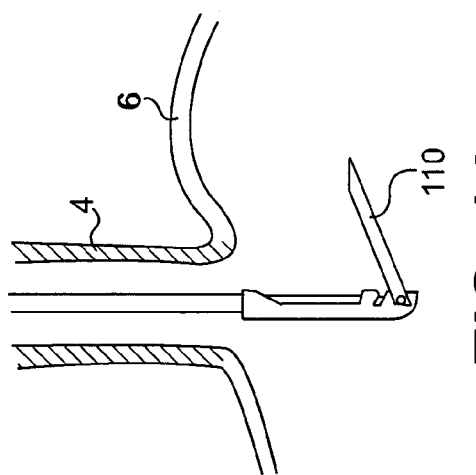
Figure 15:
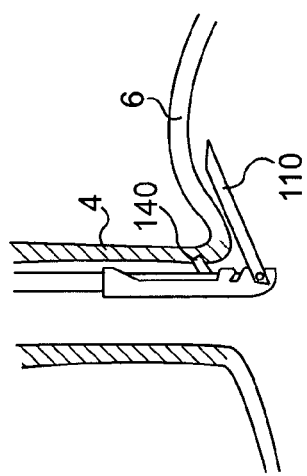
Figure 16:
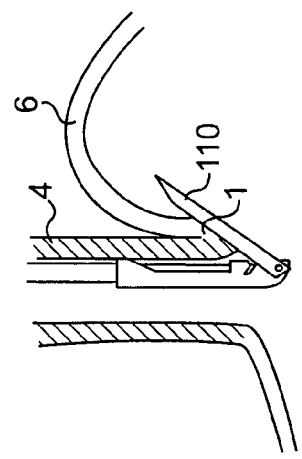

As shown in FIG. 13, the endoluminal device 10 including the tube 120 and the A-frame head 100 is inserted transorally to the gastro-esophageal junction, preferably with proper lubrication. The endoscope (not shown) is retroflexed in the stomach 7 to have viewing of the A-frame head 100. Using a manipulating device (not shown) on the proximal end of the tube 120, the folding arm 110 of the A-frame 100 extends in the stomach 7 and is positioned ready for folding, as shown in FIG. 14. The suction grasper 140 is then inserted through the tube 120 to an opening in the A-frame head 100 and suction force firmly grasps the esophageal wall 4 to prevent movement during the folding process, as shown in FIG. 15. The folding arm 110 then closes and folds the fundus wall 6 proximate to the esophagus wall 4, creating a plicated fold 1, as shown in FIG. 16. Preferably, the suction grasper is withdrawn from the A-frame head 100, and the deflector 150, 450 containing a tissue fastener 200, 300 and a needle basket 170 is inserted through a lumen of the tube 120.

Preferably, the tissue fastener 200, 300 is loaded in the deflector 150, 450, prior to the insertion. For the embodiment shown in FIGS. 7–9, the tissue fastener 200 may be loaded onto the opening 155 of the deflector 150 by inserting the slitted end of the locking mechanism 220 in the opening 155 of the deflector 150. Once the locking mechanism 220 is placed in the opening, the needle basket 170 is advanced through the conduit 157 of the deflector 150 and subsequently through the locking mechanism 220 of the fastener 200.

After the fundus wall 6 is folded proximate to the esophagus wall 4 by the folding arm 110, thereby creating a plicated fold 1 at the gastro-esophageal junction, the needle basket 170 is advanced through the conduit 157, 457, 458 of the deflector 150, 450 toward the plicated fold of the esophageal wall 4 and the fundus wall 6, held by the folding arm 110. FIGS. 17–24 schematically illustrate a method of fastening the plicated fold of the esophageal wall 4 and the fundus wall 6 with a tissue fastener 200, 300, according to an embodiment of the present invention.

As shown in FIG. 17, the needle basket 170 protrudes out of the deflector 150 and grasps the distal end 290 of the suture 250 with the grasping and releasing means 172. The needle basket 170 then carries the distal end 290 of the suture 250 from the esophageal side to the stomach side, as shown in FIG. 18. Once the needle basket 170 passes through the both walls 4, 6, the needle basket 170 releases the distal end 290 of the suture 250 and is withdrawn back into the deflector 150, as shown in FIG. 19. The plurality of locking flanges 260 help the suture 250 remain in place within the tissue layers and, preferably, only allows movement toward the stomach side. The deflector 150 containing the needle basket 170 and the locking mechanism 220 is then moved to another position within the A-frame head 100, preferably, via the slot 105 formed on the A-frame head 100, and is again advanced through the plicated fold, as illustrated by FIGS. 20 and 21. Once through to the stomach side, the grasping and releasing means 172 in the needle basket 170 is used again to grasp the loose distal end 290 of the suture 250. By pulling the needle basket 170 back into the deflector 150, shown in FIG. 22, the distal end 290 of the suture 250 engages the locking mechanism 220 and a closed loop of the tissue fastener 200 is created. By continuously pulling the needle basket 170 and/or by withdrawing the deflector 150, the fastening tension of the tissue fastener 200 can be further tightened. Once the desired fastening tension is achieved, the needle basket 170 releases the suture 250 and is removed together with the deflector 150. The installed tissue fastener 200 is shown in FIG. 23. For the tissue fastener 300 shown in FIGS. 10–12, after the tissue fastener is installed in place, the distal portion 480 of the deflector 450 is detached from the main body, as shown in FIG. 24. If desired, additional tissue fasteners 200, 300 may be placed by repeating the method described above.

Figure 25:
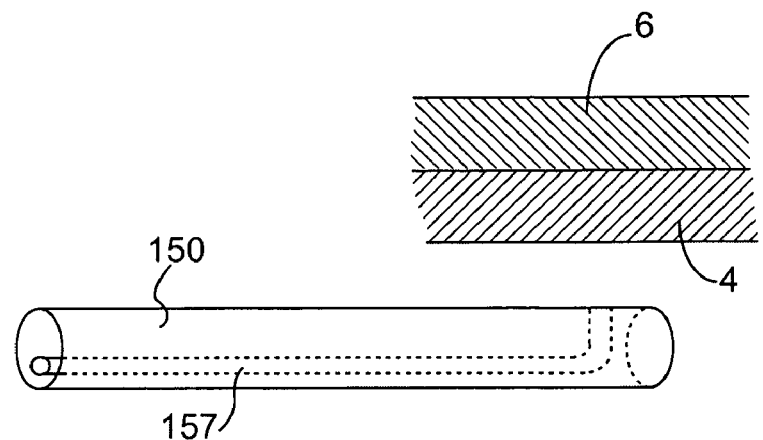
FIGS. 25–32 are schematic illustrations of a method of fastening multiple tissue layers, according to another embodiment of the present invention.
Figure 26:
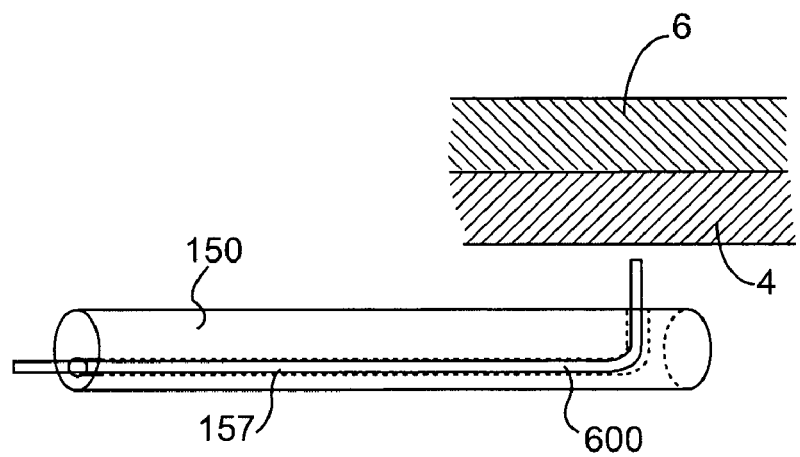
Figure 27:
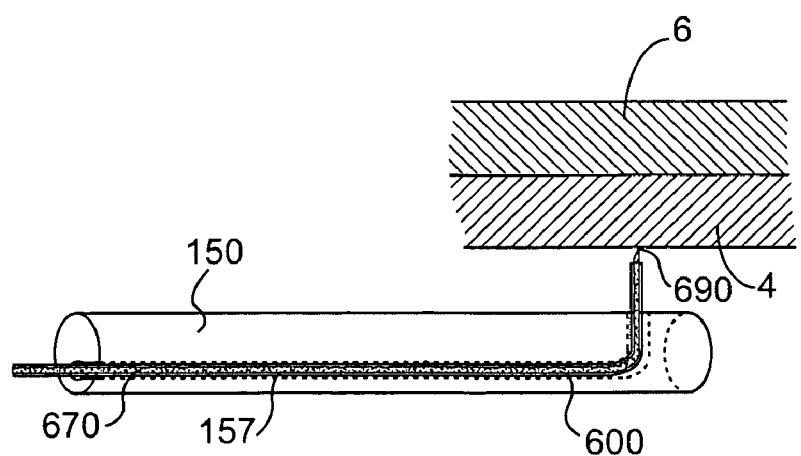

Another method for installing a tissue fastener using a deflector system 150, according to another aspect of the invention, is described below with reference to FIGS. 25–32. As shown in FIG. 25, after the fundus wall 6 is folded proximate to the esophageal wall 4, a deflector 150 is inserted proximate to the plicated fold of the esophageal wall 4 and the fundus wall 6. A flexible trocar tube 600 is then inserted through the conduit 157 of the deflector 150 and is deflected toward the plicated fold, as shown in FIG. 26. Preferably, an introducer 670 or a needle having a sharp cutting edge 690 and a point at its distal end is inserted through the trocar tube 600 to perforate through the plicated fold, as shown in FIG. 27. Instead of using an introducer 670, it should be recognized that the trocar tube 600 may include a sharp cutting edge at its distal end and, thereby, eliminating the need for the introducer 670.

Figure 28:
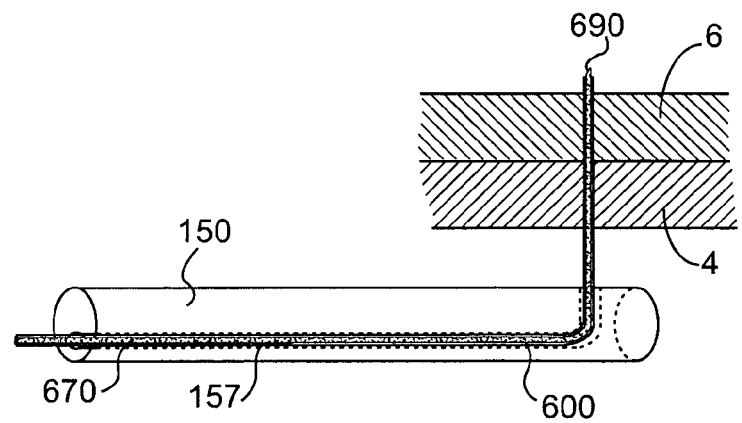
Figure 29:
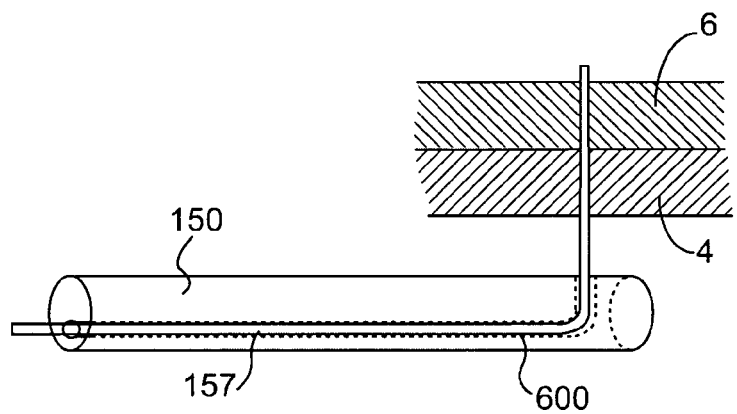

As shown in FIG. 28, the trocar tube 600 with the introducer 670 passes through the plicated fold of the esophageal wall 4 and the fundus wall 6. Once the trocar tube 600 passes through the plicated fold, the introducer 670 is withdrawn from the trocar tube 600 while the trocar tube 600 remains in the same place, as shown in FIG. 29. A tissue fastener 800 with its proximal end grasped by a grasper-pusher assembly 700 is inserted through the trocar tube 600. The grasper-pusher assembly 700 includes a grasper 710 at its distal end.

The tissue fastener 800 has a distal member 810, a proximal member 890, and a connecting member 850 connecting the distal and proximal members 810, 890 to each other. Preferably, the distal member 810 and the proximal member 890 are each constructed to expand from a contracted state to an expanded state, such that, when protruded out of the trocar tube 600, each of the distal and proximal members 810, 890 expands to form a fastening member for holding the esophageal wall 4 and the fundus wall 6 together. In the contracted state, the tissue fastener 800 is low in profile to be loaded into the trocar tube 800.

Figure 30:
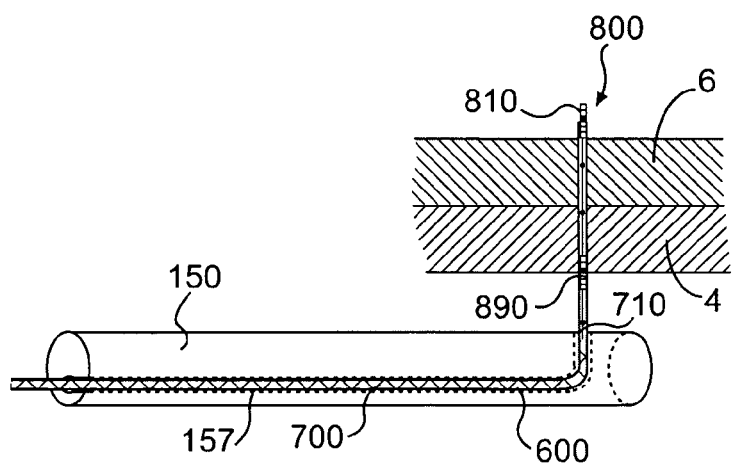
Figure 31:
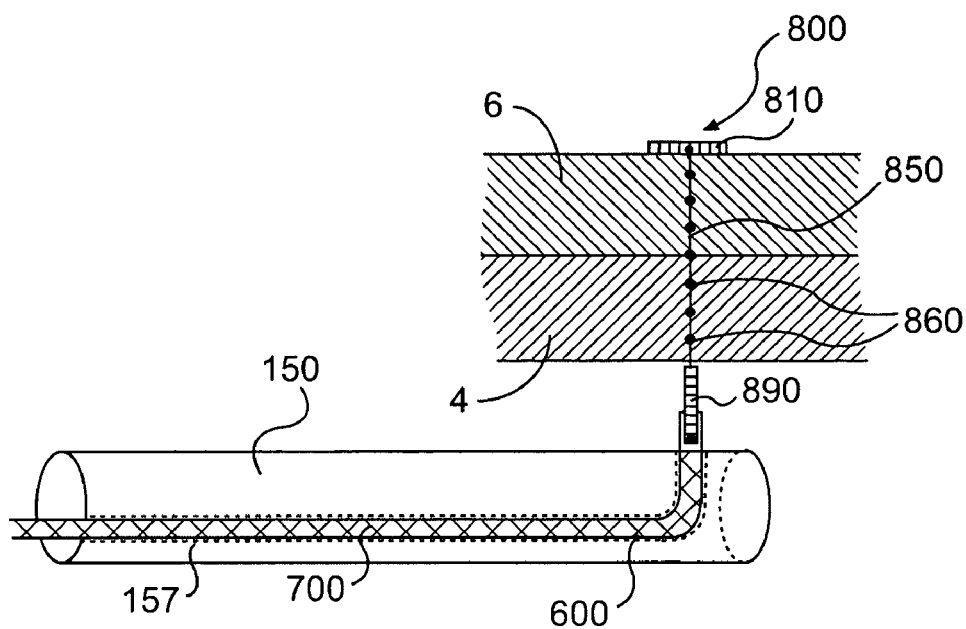
Figure 32:
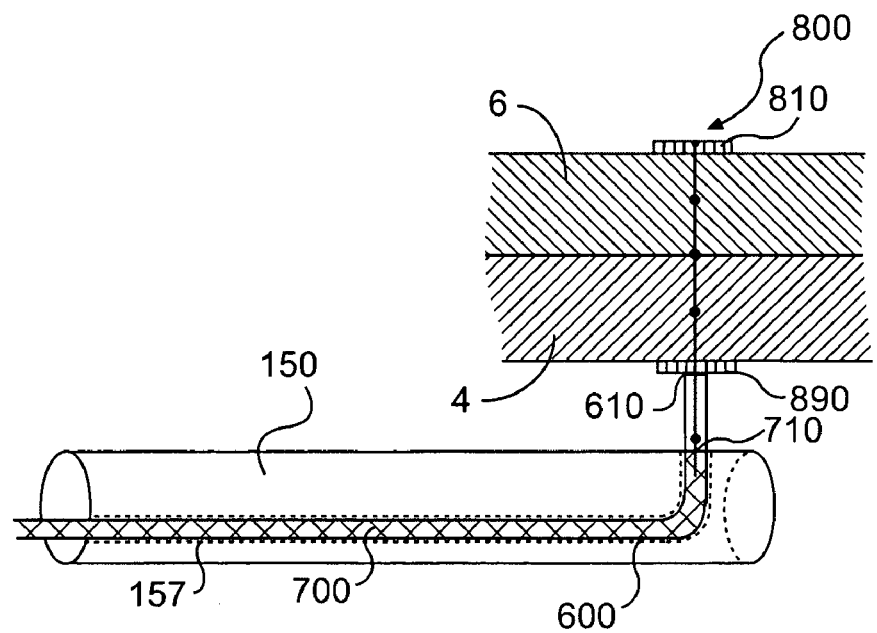

In an embodiment shown in FIGS. 30–32, each of the distal and proximal members 810, 890 is a T-shaped fastening button connected to a connecting member, e.g., a suture 850. While the distal member 810 is fixedly secured to a distal end of the suture 850, the proximal member 890 is configured to move axially along the suture 850, so that the fastening tension can be adjusted. As shown in FIG. 31, when the distal member 810 is advanced out of the trocar tube 600, the distal member falls into the stomach 7 and, when the distal member 810 is pulled back by pulling the suture 850, the T-shaped fastening button is formed and fastens the plicated fold against the fundus wall 6. Once the distal member 810 is properly positioned, the trocar tube 600 is withdrawn, while keeping the grasper-pusher 700 in the same position, to expose the proximal member 890 out of the trocar tube 600. Similar to the distal member 810, when the proximal member 890 is out of the trocar tube 600, the proximal member 890 extends to form a T-shaped fastening button. After the proximal fastening button 890 is formed, the grasper-pusher assembly 700 is pulled, while the trocar tube 600 pushes the proximal fastening button 890 toward the esophageal wall 4, to adjust the tightness of the tissue fastener 800, as shown in FIG. 32. Preferably, the suture 850 includes a plurality of locking members 860 associated with the proximal fastening button 890 for locking the button in place. The locking members 860 allow the proximal member 890 to remain in place, and thereby prevent tissue fastener migration. Although a specific embodiment of a tissue fastener 800 is used to illustrate a method of fastening multiple tissue layers, it should be recognized that any other suitable designs of tissue fasteners having the similar operational characteristics may be utilized. Moreover, it should also be recognized that the disclosed tissue fastener 800 may be used with any other suitable deployment mechanisms known in the art.

Once the desired fastening tension is achieved, the grasper-pusher assembly 700 releases the proximal end of the suture 850 and is removed together with the trocar tube 600 out of the body. The remaining portion of the suture 850 beyond the proximal fastening member 890 may be cut off by using a suitable device. Depending on the type of tissue fasteners used and the desired fastening strength, additional tissue fasteners 800 may be placed by repeating the method described above.

Although the present invention is depicted in this disclosure as being used in the treatment of GERD, e.g., a fundoplication procedure performed in the gastro-esophageal junction, it is to be understood that the tissue fastener and related deployment methods and systems of the present invention can be used to treat any of a number of different disease conditions, and can be used for fastening any desired body tissues.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoluminal surgical device for fastening multiple tissue layers, comprising:
   a tissue fastener;
   a flexible needle having means for grasping and releasing a portion of the tissue fastener;
   a deflector for deflecting and guiding the needle toward the multiple tissue layers; and
   a flexible tube having at least one lumen and configured to extend from outside of a body to inside the body, wherein the tube is configured to accommodate the tissue fastener, the flexible needle, and the deflector inside the lumen during delivery.

2. The surgical device as defined in claim 1, wherein the deflector includes an elongated tube.

3. The surgical device as defined in claim 2, wherein the deflector defines a conduit therein for guiding the needle, wherein the conduit is curved to deflect and guide the needle toward the multiple tissue layers.

4. The surgical device as defined in claim 3, wherein the conduit includes a proximal portion and a distal portion, the proximal portion extending substantially axially within the deflector and the distal portion angled relative to the proximal portion.

5. The surgical device as defined in claim 4, wherein the distal portion is substantially perpendicular to the proximal portion of the deflector.

6. The surgical device as defined in claim 4, wherein the distal portion communicates with an opening defined by a side surface of the deflector.

7. The surgical device as defined in claim 4, wherein:
   the deflector includes a main body and a distal body releaseably connected to the main body, wherein the main body contains the proximal portion of the conduit and the distal body contains the distal portion of the conduit.

8. The surgical device as defined in claim 1, further comprising an A-frame head configured to receive the deflector and move axially relative to the deflector.

9. The surgical device as defined in claim 8, wherein the A-frame head includes a slot for guiding the deflector.

10. The surgical device as defined in claim 8, wherein the A-frame head includes a foldable arm having an opening.

11. The surgical device as defined in claim 1, wherein the needle is configured to move relative to the deflector.

12. The surgical device as defined in claim 1, wherein the needle includes a cutting edge at a distal end of the needle for perforating through the multiple tissue layers.

13. The surgical device as defined in claim 1, wherein the deflector defines an opening in a side of the deflector configured to receive the tissue fastener and the needle.

14. The surgical device as defined in claim 13, wherein the tissue fastener comprises:
   a flexible suture having a distal end and a proximal end; and
   a locking mechanism for interconnecting the distal and proximal ends of the suture to form the suture into a closed loop.

15. The surgical device as defined in claim 14, wherein the tissue fastener further includes means for attaching the tissue fastener to the opening of the deflector.

16. The surgical device as defined in claim 15, wherein the means for aching includes sib In the iocldng mechanism.

17. The surgical device as defined in claim 14, wherein the locking mechanism has conical shape.

18. The surgical device as defined in claim 1, further comprising an A-frame head coupled to a distal portion of the tube, the A-frame head including an arm pivotally connected to a portion of the A-frame head and configured to receive the multiple tissue layers between the arm and a surface of the A-frame head.

19. The surgical device as defined in claim 1, further comprising a grasper device for grasping at least one tissue layer.

20. An endoluminal surgical device for fastening multiple tissue layers, comprising:
   a tissue fastener;
   a flexible needle having a grasper for grasping a portion of the tissue fastener; and
   a deflector for deflecting and guiding the needle toward the multiple tissue layers,
   wherein the grasper comprises:
      a suction hole proximate a distal end of the flexible needle; and
      a suction conduit formed inside the flexible needle,
      wherein the suction hole is configured to receive the portion of the tissue fastener into and out of the suction hole during operation.

21. An endoluminal surgical device for fastening multiple tissue layers, comprising:
   a tissue fastener;
   a flexible needle having means for grasping and releasing a portion of the tissue fastener;
   a deflector for deflecting and guiding the needle toward the multiple tissue layers; and
   an A-frame head configured to receive the deflector and move axially relative to the deflector.

22. The surgical device as defined in claim 21, wherein the A-frame head includes a slot for guiding the deflector.

23. The surgical device as defined in claim 21, wherein the A-frame head includes a foldable arm having an opening.

24. An endoluminal surgical device for fastening multiple tissue layers, comprising:
- a tissue fastener;
- a flexible needle having means for grasping and releasing a portion of the tissue fastener; and
- a deflector for deflecting and guiding the needle toward the multiple tissue layers;
- wherein the deflector defines a conduit therein for guiding the needle, the conduit is curved to deflect and guide the needle toward the multiple tissue layers, and the conduit includes a proximal portion and a distal portion, the proximal portion extending substantially axially within the deflector and the distal portion angled relative to the proximal portion, and
- wherein the distal portion communicates with an opening defined by a side surface of the deflector.

25. An endoluminal surgical device for fastening multiple tissue layers, comprising:
- a tissue fastener;
- a flexible needle having means for grasping and releasing a portion of the tissue fastener; and
- a deflector for deflecting and guiding the needle toward the multiple tissue layers;
- wherein the deflector defines a conduit therein for guiding the needle, the conduit is curved to deflect and guide the needle toward the multiple tissue layers, and the conduit includes a proximal portion and a distal portion, the proximal portion extending substantially axially within the deflector and the distal portion angled relative to the proximal portion, and
- wherein the deflector includes a main body and a distal body releaseably connected to the main body, wherein the main body contains the proximal portion of the conduit and the distal body contains the distal portion of the conduit.

26. An endoluminal surgical device for fastening multiple tissue layers, comprising:
- a tissue fastener;
- a flexible needle having means for grasping and releasing a portion of the tissue fastener; and
- a deflector for deflecting and guiding the needle toward the multiple tissue layers,
- wherein the deflector defines an opening in a side of the deflector configured to receive the tissue fastener and the needle.

27. The surgical device as defined in claim 26, wherein the tissue fastener comprises:
- a flexible suture having a distal end and a proximal end; and
- a locking mechanism for interconnecting the distal and proximal ends of the suture to form the suture into a closed loop.

28. The surgical device as defined in claim 27, wherein the tissue fastener further includes means for attaching the tissue fastener to the opening of the deflector.

29. The surgical device as defined in claim 28, wherein the means for attaching includes slits in the locking mechanism.

30. The surgical device as defined in claim 27, wherein the locking mechanism has a conical shape.

* * * * *

UNITED STATES PATENT AND TRADEMARK OFFICE
CERTIFICATE OF CORRECTION

| | | |
|---|---|---|
| PATENT NO. | : 7,125,413 B2 | Page 1 of 1 |
| APPLICATION NO. | : 10/175307 | |
| DATED | : October 24, 2006 | |
| INVENTOR(S) | : Sergey S. Grigoryants et al. | |

It is certified that error appears in the above-identified patent and that said Letters Patent is hereby corrected as shown below:

Claim 16, column 12, line 29, "whereIn" should read --wherein--.

Claim 16, column 12, line 30, "aching includes sib In the iocldng" should read --attaching includes slits in the locking--.

Claim 17, column 12, line 31, "whereIn" should read --wherein--.

Claim 17, column 12, line 32, "has conical" should read --has a conical--.

Signed and Sealed this

Ninth Day of January, 2007

JON W. DUDAS
*Director of the United States Patent and Trademark Office*